United States Patent [19]

Swain et al.

[11] Patent Number: 5,584,861
[45] Date of Patent: Dec. 17, 1996

[54] DEVICE FOR USE IN SECURING A THREAD

[75] Inventors: Paul Swain; Feng Gong; Geoffrey J. Brown; Timothy N. Mills, all of London, United Kingdom

[73] Assignee: University College London, London, England

[21] Appl. No.: 397,156

[22] PCT Filed: Sep. 3, 1993

[86] PCT No.: PCT/GB93/01860

§ 371 Date: Apr. 4, 1995

§ 102(e) Date: Apr. 4, 1995

[87] PCT Pub. No.: WO93/08747

PCT Pub. Date: May 13, 1993

[30] Foreign Application Priority Data

Sep. 4, 1992 [GB] United Kingdom ................. 9218754

[51] Int. Cl.⁶ .................................................. A61B 17/00
[52] U.S. Cl. ...................... 606/232; 606/148; 606/151; 606/142; 227/902
[58] Field of Search ......................... 606/151, 157, 606/158, 148, 232, 139, 142, 143; 227/902; 24/136 R

[56] References Cited

U.S. PATENT DOCUMENTS

| 4,235,238 | 11/1980 | Ogiu. | |
| 4,741,330 | 5/1988 | Hayhurst. | |
| 4,750,492 | 6/1988 | Jacobs | 606/232 |
| 5,364,407 | 11/1994 | Poll | 606/232 |
| 5,366,459 | 11/1994 | Yoon | 606/157 |

FOREIGN PATENT DOCUMENTS

WOA9308747 5/1993 WIPO.

Primary Examiner—Michael Powell Buiz
Assistant Examiner—Jeffrey A. Schmidt
Attorney, Agent, or Firm—Darby & Darby, P.C.

[57] ABSTRACT

A device for use in securing a thread includes a tube having a distal end and a proximal end. The tube defines a recess at the distal end to receive therein a sleeve having a cavity in which a plug is removably inserted. The device further includes a generally U-shaped stirrup that is movably connected to the tube. The U-shaped stirrup is movable between a first position in which the base of the U holds the sleeve and plug in the recess and a second position in which the sleeve and plug are free to leave the recess. The base of the U is continuous.

14 Claims, 1 Drawing Sheet

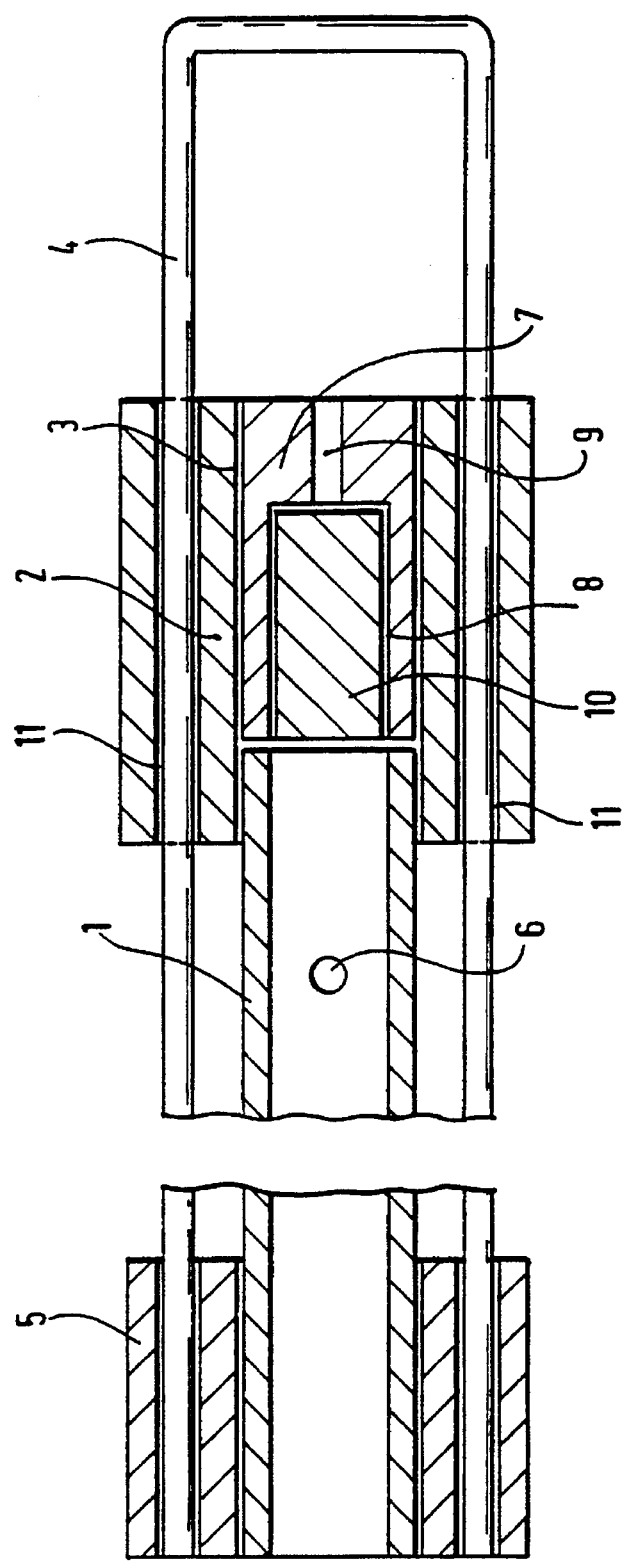

DEVICE FOR USE IN SECURING A THREAD

This application is a 371 of PCT/6B93/01860 filed Sep. 3, 1993 which was filed off of United Kingdom 9218754.1 filed Sep. 4, 1992.

BACKGROUND OF THE INVENTION

This invention relates to a device for use in securing a thread. It is particularly intended for use in securing threads in surgery, and more particularly in surgery carried out using an endoscope, notably a flexible endoscope.

It has hitherto proved difficult to secure threads by knotting during flexible endoscopy. In effect, the surgeon is operating down a single longitudinally extending channel, and in endeavouring to tie a knot the surgeon encounters the problem that an effective knot generally requires the application of force along a direction transverse to the channel of the endoscope. The present invention aims to provide a solution to that problem.

SUMMARY OF THE INVENTION

According to the present invention there is provided a device for use in securing a thread, which comprises a tube provided with means defined at one end thereof for receiving therein a sleeve having a cavity in which a plug is insertable.

An embodiment of the invention is shown diagrammatically in the accompanying drawings, which is a longitudinal section. It should be emphasised that the drawing is not to scale.

BRIEF DESCRIPTION OF THE DRAWING

The sole FIGURE is a cross-sectional view of a device for securing a thread according to the present invention.

DETAILED DESCRIPTION OF THE PREFERRED EMBODIMENT

The device comprises a tube 1, which is preferably a flexible tube. At the distal end, i.e. the end which is to be inserted into the patient, an overtube 2 is fixedly secured to the tube 1 to define a recess 3. Extending along the outside of the tube 1, and over the end of the overtube 2, is a U-shaped stirrup 4. The stirrup may be made, for example, of a stainless steel wire. The stirrup is longitudinally slidable with respect to the tube 1, and the arms of the stirrup pass through respective guide passages 11. To enable sliding to be effected the proximal end of the stirrup is secured to a slide member 5 which can be grasped and moved by the user. In addition to the guide passageway 11, other means (not shown) are provided along the length of the outside of the tube, within which the stirrup is slidable, so as to prevent the stirrup from slipping off the tube. Near its distal end, the tube 1 is provided with a pair of apertures 6 each of which has a diameter substantially greater than the diameter of the surgical thread with which the device is to be used. One of the apertures is visible in the drawing. The other is diametrically opposite to it. The purpose of the apertures 6 will become apparent from the description below of the use of the device.

The recess 3 serves to receive an elongate sleeve 7. The sleeve defines within it a cavity 8. The cavity 8 is open at one end to the end of the tube 1, and, although not shown, at that end the cavity is preferably chamfered. The other end of the cavity 8 communicates with the other end of the sleeve 7 by a passage 9. The stirrup 4 is offset with respect to the longitudinal axis of the tube 2, with which the passage 9 is aligned, so that when the stirrup is moved leftwards with respect to the tube it does not foul the end of the passage 9. The passage is smaller in diameter than the cavity 8, but large enough to permit the surgical thread to pass therethrough. A plug 10 is located in the cavity 8, the plug being of a size such that it can slide down the interior of the tube 1. The sleeve 7 is removable from the recess 3, and the plug 10 is removable from the cavity 8, and at the start of the procedure in which the device is used, the sleeve 7 and plug 10 are separate from one another and from the remainder of the device.

Prior to the thread-securing procedure in which the device of the present invention is used, the surgeon has carried out a surgical procedure in which a thread has been passed through the tissue of the patient, and the ends of the thread now need to be secured. It is assumed for present purposes that the ends of the thread are outside the patient, and if surgery has been carried out using an endoscope then the ends of the thread will generally emerge through the mouth or anus. With the stirrup 4 in the position shown in the drawings, a sleeve 7 is inserted in the recess 3. At this point there is no plug in the cavity 8. The stirrup 4 is then moved leftwards, as viewed in the drawing, so that the sleeve is held in place in the recess by the stirrup. The ends of the thread are then introduced into the passage 9 from the distal end, and passed through the cavity 8 into the end of the tube 1, and each then exits the tube through a respective aperture 6. Instead of a pair of apertures it would alternatively be possible to use a single aperture, in which case both thread ends would pass through it. The whole device is then inserted into the patient until the distal end thereof is located adjacent the point at which the thread passes through the patient's tissue. During this insertion process the ends of the thread continue to be held outside the patient, so that, in effect, the end of the device slides down the thread. Preferably, the device is sufficiently small as to enable it to pass down the operating channel of flexible endoscope, for example the endoscope which has been used in carrying out the surgery described above.

When the end of the device is at the desired location, the plug 10 is introduced into the proximal end of the tube 1, and is pushed down the tube and into the cavity 8 by a flexible pusher rod (not shown). Entry of the plug into the cavity is assisted if the cavity is being chamfered, as mentioned above. As the plug enters the cavity 8 it traps the thread against the internal wall of the plug, and friction between the sleeve 7, the plug 10 and the thread holds these elements together. If desired, the cavity 8 can taper as viewed from left to right.

The stirrup 4 is then moved to its extended position shown in the drawing, and the tube 1, with the overtube 2 and stirrup 4, is removed from the patient. The sleeve 7 and plug 10 remain attached to the thread, and thus leave the recess 3 when the removal step just described takes place. During removal, the ends of the thread slide back through the aperture 6. The end portions of the thread can be severed on the side of the sleeve/plug combination remote from the tissue, by a severing operation.

After the procedure just described, the sleeve/plug combination remains in the patient, holding the ends of the thread to prevent their withdrawal through the tissue in which the thread has been inserted. If it were desired that the sleeve/plug combination should no longer be present after the need for it had passed, the sleeve and plug could be formed of a material was which slowly soluble. Otherwise, the plug and sleeve may be made, for example, of a surgically acceptable, inert plastics material.

What is claimed is:

1. A device for use in securing a thread, which comprises a tube having a distal end and a proximal end and provided with receiving means defining a recess at said distal end receiving therein a sleeve having a cavity in which a plug is removably inserted, the device further comprising a generally U-shaped stirrup movably connected to said tube, and movable between a first position in which the base of the U holds said sleeve and plug in the said recess and a second position in which the sleeve and plug are free to leave the recess, said base of the U being continuous.

2. A device according to claim 1, wherein the tube is provided at a location between said receiving means, and said proximal end with at least one aperture extending through the wall of the tube to enable the thread to pass therethrough.

3. A device according to claim 2, wherein the tube has a pair of said apertures at diametrically opposed locations.

4. A device according to claim 1, wherein said sleeve has a passage through which said cavity is open to the distal end of the sleeve, the passage being such that the plug cannot pass therethrough.

5. A device according to claim 4, wherein the said base of the U is offset with respect to said passage.

6. A device according to claim 1, wherein the stirrup is attached to a slide member which is free to slide with respect to said tube and which can be so slid by a user.

7. A device according to claim 1, wherein the tube is provided with means for guiding said stirrup in its movement between said first and second positions.

8. A device according to claim 1, wherein said receiving means comprises an overtube secured over the distal end portion of said tube.

9. A device according to claim 1, wherein the cavity is open at the proximal end of said sleeve via an opening of sufficient size to allow the plug to enter the cavity through said opening during insertion of the plug therein.

10. A device for use in securing a thread, which comprises a tube having a distal end and a proximal end and provided with receiving means defining a recess at said distal end receiving therein a sleeve having a cavity in which a plug is removably inserted, the device further comprising a generally U-shaped stirrup movably connected to said tube, and movable between a first position in which the base of the U holds said sleeve and plug in the said recess and a second position in which the sleeve and plug are free to leave the recess, the tube being provided at a location between said receiving means, and said proximal end with at least one aperture extending through the wall of the tube to enable the thread to pass therethrough.

11. A device according to claim 10, wherein the tube has a pair of said apertures at diametrically opposed locations.

12. A device for use in securing a thread, which comprises a tube having a distal end and a proximal end and provided with receiving means defining a recess at said distal end receiving therein a sleeve having a cavity in which a plug is removably inserted, the device further comprising a generally U-shaped stirrup movably connected to said tube, and movable between a first position in which the base of the U holds said sleeve and plug in the said recess and a second position in which the sleeve and plug are free to leave the recess, said sleeve having a passage through which said cavity is open to the distal end of the sleeve, the passage being such that the plug cannot pass therethrough.

13. A device according to claim 12, wherein the said base of the U is offset with respect to said passage.

14. A device for use in securing a thread, which comprises a tube having a distal end and a proximal end and provided with receiving means defining a recess at said distal end receiving therein a sleeve having a cavity in which a plug is removably inserted, the device further comprising a generally U-shaped stirrup movably connected to said tube, and movable between a first position in which the base of the U holds said sleeve and plug in the said recess and a second position in which the sleeve and plug are free to leave the recess, said receiving means comprising an overtube secured over the distal end portion of said tube.

* * * * *